United States Patent
Ermantraut et al.

(10) Patent No.: US 7,262,842 B2
(45) Date of Patent: Aug. 28, 2007

(54) DEVICE FOR REFERENCING FLUORESCENCE SIGNALS

(75) Inventors: Eugen Ermantraut, Jena (DE); Thomas Kaiser, Bucha (DE); Jens Tuchscheerer, Jena (DE)

(73) Assignee: Clondiag Chip Technologies GmbH, Jena (DE)

(*) Notice: Subject to any disclaimer, the term of this patent is extended or adjusted under 35 U.S.C. 154(b) by 399 days.

(21) Appl. No.: 10/472,974

(22) PCT Filed: Mar. 20, 2002

(86) PCT No.: PCT/EP02/03140

§ 371 (c)(1),
(2), (4) Date: May 24, 2004

(87) PCT Pub. No.: WO02/077620

PCT Pub. Date: Oct. 3, 2002

(65) Prior Publication Data
US 2004/0196455 A1    Oct. 7, 2004

(30) Foreign Application Priority Data
Mar. 28, 2001 (DE) ............... 101 15 752
Jan. 11, 2002 (DE) ............... 102 00 865

(51) Int. Cl.
*G01J 1/10* (2006.01)
*G01D 18/00* (2006.01)

(52) U.S. Cl. .............. 356/243.1; 250/252.1; 250/458.1

(58) Field of Classification Search .. 356/243.1–243.8, 356/317, 318; 428/327, 349; 257/414, 431; 250/252.1, 458.1
See application file for complete search history.

(56) References Cited

U.S. PATENT DOCUMENTS

| 4,302,678 | A | * | 11/1981 | Schiffert ............ 250/461.1 |
| 5,040,047 | A | * | 8/1991 | Cole et al. ............ 257/642 |
| 5,110,833 | A | | 5/1992 | Mosbach |
| 5,310,648 | A | | 5/1994 | Arnold et al. |
| 5,372,519 | A | | 12/1994 | Chen |
| 5,384,261 | A | * | 1/1995 | Winkler et al. ........ 436/518 |
| 5,412,087 | A | * | 5/1995 | McGall et al. ........ 536/24.3 |
| 5,414,258 | A | | 5/1995 | Liang |

(Continued)

FOREIGN PATENT DOCUMENTS

| DE | 19612356 | 10/1997 |
| EP | 0235726 | 9/1987 |
| EP | 0915174 | 5/1999 |

(Continued)

*Primary Examiner*—Layla G. Lauchman
(74) *Attorney, Agent, or Firm*—Steptoe & Johnson LLP

(57) ABSTRACT

The invention relates to a device for referencing fluorescence signals and/or calibration of fluorescence detection systems, whereby the device comprises an essentially non-fluorescing support, on which are applied polymer layers in several defined regions and with partly varying thicknesses and/or compositions. Said polymer layers are applied to the support such as to fluoresce after corresponding irradiation and the device may thus be used as a fluorescence standard. The invention further relates to a method for the production of said fluorescence standards.

53 Claims, 9 Drawing Sheets

U.S. PATENT DOCUMENTS

| | | |
|---|---|---|
| 5,453,199 A | 9/1995 | Afeyan et al. |
| 5,461,175 A | 10/1995 | Fischer et al. |
| 5,541,342 A | 7/1996 | Korhonen et al. |
| 5,587,273 A | 12/1996 | Yan et al. |
| 5,658,734 A | 8/1997 | Brock et al. |
| 5,838,435 A | 11/1998 | Sandison .................... 356/273 |
| 6,040,047 A | 3/2000 | Yamashita |
| 6,040,138 A | 3/2000 | Lockhart et al. |
| 6,472,671 B1 * | 10/2002 | Montagu ................. 250/458.1 |
| 6,794,424 B2 * | 9/2004 | Holcomb et al. ........... 523/137 |
| 7,053,384 B2 * | 5/2006 | Schmid et al. ........... 250/458.1 |

FOREIGN PATENT DOCUMENTS

| | | |
|---|---|---|
| JP | 60257136 | 12/1985 |
| JP | 61281904 | 12/1986 |
| JP | 1010249 | 1/1989 |
| JP | 2069640 | 3/1990 |
| WO | WO90/03382 | 4/1990 |
| WO | WO98/49537 A1 | 11/1998 |
| WO | WO 01/06227 A2 | 1/2001 |
| WO | WO 01/06227 A3 | 1/2001 |

* cited by examiner

DEVICE FOR REFERENCING FLUORESCENCE SIGNALS

BACKGROUND OF THE INVENTION

1. Field of the Invention

The invention relates to a device which makes it possible to compare the imaging characteristics and signal sensitivity of fluorescence detection systems and enables test-specific referencing of fluorescence signals. The invention also relates to a method for producing said device.

2. Description of the Related Technology

Frequently, biomedical tests are based on the detection of an interaction between a molecule or an affinity matrix whose identity or whose constitution is known (probe) and an unknown molecule to be detected, or unknown molecules to be detected (target molecule or target).

In modern tests, the probes, if they are molecules, are frequently immobilised on carriers in the form of a substance library in known quantity and position. Such devices are also called probe arrays or chips. Typically, a probe array comprises several so-called array elements which are the regions of a probe array in which a particular molecular probe is frequently immobilised in multiple copy. The sum of all occupied array elements thus constitutes the probe array.

Immobilisation of molecular probes in the form of a substance library on probe arrays makes it possible to analyse in parallel on several probes concurrently a sample which contains the target molecules to be detected. This makes possible a systematic analysis with a high throughput in a short time (high throughput screening, D. J. Lockhart, E. A. Winzeler, Genomics, Gene Expression and DNA Arrays, Nature 2000, 405, 827-836). For the purpose of producing the probe arrays, the probes are usually immobilised in a specified way on a suitable matrix, as described for example in WO 00/12575 (see e.g. U.S. Pat. No. 5,412,087, WO 98/36827) or synthetically produced (see e.g. U.S. Pat. No. 5,143,854).

In principle, furnishing proof of an interaction between the probe and the target molecule occurs as follows:

The probe or probes are attached in the specified way to a particular matrix in the form of a probe array. Subsequently, in a solution, the targets are brought into contact with the probes and incubated at defined conditions. If, due to complementary characteristics, the probe and the target molecule have an affinity to each other, then a specific interaction between the probe and the target takes place during incubation. The bond which occurs during this process is clearly more stable than the bond of target molecules on probes which are not specific to the target molecule. In order to remove non-specifically bonded target molecules, the system is washed with respective solutions, or heated, or is subjected to measures which have a correspondingly restrictive effect.

Furnishing proof of the specific interaction between a target and its probe can then be carried out by way of a multitude of methods which as a rule depend on the type of marker, such marker, depending on the design of the experiment, having been introduced into the target molecules or into the probe molecules during or after the interaction between the target molecule and the probe array. Such markers can for example include fluorescent groups, radioactive markers, enzymes or chemiluminescent molecules, with the method of proof to be used being governed by the type of marker (A. Marshall, J. Hodgson, DNA Chips: An Array of Possibilities, Nature Biotechnology 1998, 16, 27-31; G. Ramsay, DNA Chips: State of the Art, Nature Biotechnology 1998, 16, 40-44).

Depending on the substance library immobilised on the probe array, and depending on the chemical nature of the target molecules, by means of this test principle, interactions between nucleic acids, between proteins, and between nucleic acids and proteins can be investigated (for an overview, see F. Lottspeich, H. Zorbas, 1998, "Bioanalytik", Spektrum Akademischer Verlag, Heidelberg/Berlin).

The following can be considered as possible substance libraries which can be immobilised on probe arrays or chips: antibody libraries, receptor libraries, peptide libraries and nucleic acid libraries. Nucleic acid libraries assume far and away the most important role, with DNA molecule libraries or RNA molecule libraries being used particularly frequently. In this context, probe-array-based analysis of interactions between nucleic acids follows the principles of the nucleic acid hybridisation technique (A. A. Leitch, T. Schwarzacher, D. Jackson, I. J. Leitch, 1994, "In vitro-Hybridisierung", Spektrum Akademischer Verlag, Heidelberg/Berlin/Oxford).

Usually, proof of specific interactions between a probe and a target is furnished by fluorescence-optical evaluations because they are characterised by good sensitivity, versatility concerning the markers that can be used, and by the possibility of location-resolved and time-resolved detection of the interaction with comparatively little expenditure (above all in comparison with mass-spectroscopy methods) as well as by the elimination of irradiation exposure, the latter occurring when radioactive marking reagents are used. In addition, depending on the fluorophores used for marking, the excitation wavelength range and the detection wavelength range can be set.

However, in practical application, qualitative and quantitative fluorescence-optical evaluations are negatively affected by a number of factors connected to fluorescence spectroscopy per se, to the type of the fluorescence markers selected, and to the type and construction of the detection systems used. Such factors include above all non-specific background signals (signal noise) which arise as a result of intrinsic optical characteristics of the fluorescence markers (e.g. bleaching, quenching or fluorescence quenching of the dyes used); as a result of the physical-chemical characteristics of the probe or of the targets and their solutions (e.g. autofluorescence); as a result of fluctuations in the optical system (e.g. irradiation intensity of the light source, and extraneous light); and as a result of the construction and type of the detection systems used (e.g. autofluorescence of the assembly elements, capability of the detectors for spatial and temporal resolution, scattering, reflections).

Any assessment as to whether a measured fluorescence intensity represents a signal or merely forms part of signal noise thus requires elimination or minimisation of disturbing influences, as well as the use of devices and methods which make referencing of the measured fluorescence signals possible. Such devices are also referred to as a fluorescence calibration standard.

Efforts to minimise device-related signal noise result in very considerable technical expenditure on the construction of highly sensitive detectors which make possible both qualitative and quantitative evaluation of fluorescence signals. In particular, for evaluation during high throughput screening of probe arrays, which evaluation necessitates a certain degree of automation, specially adapted detection systems are required.

Fluorescence-optical read-outs of molecular probe arrays by means of standard epifluorescence structures, e.g. CCD (Charge Coupled Device) based detectors are used which for the purpose of qualitative differentiation of optical effects (scattering, reflection) achieve excitation of the fluorophores in the dark field (by way of reflected-light microscopy or transmitted-light microscopy) (C. E. Hooper et al., Quantitive Photone Imaging in the Life Sciences Using Intensified CCD Cameras, Journal of Bioluminescence and Chemiluminescence 1990, 337-344). In this process, imaging of the probe arrays takes place either by exposure or by rastering with the use of high-resolution optics. Complicated illumination optics and filter systems are necessary for minimising occurring autofluorescence, or for providing system-inherent optical effects such as illumination homogeneity, across the entire probe array.

Confocal scanning systems (described in U.S. Pat. No. 5,304,810) make it possible to evaluate fluorescence signals from selected planes of a sample. They are based on selecting the fluorescence signals along the optical axis by means of pinholes, which results in very considerable adjustment effort in relation to the samples, as well as necessitating the establishment of a powerful autofocus system. The technical implementation of such systems is highly complex, and the required components which include lasers, pinholes, (cooled) detectors (e.g. PMT, avalanche diodes, CCD systems), high-precision mechanical translation elements and optics, have to be integrated and optimised in relation to each other at considerable expense (described in U.S. Pat. Nos. 5,459,325, 5,192,980, 5,834,758).

Thus, detection systems are known with which the molecular interaction of a target comprising a fluorescence marker and a specific probe, as occurs e.g. in probe-array-based experiments, can be detected. Despite the very considerable technical expenditure described, which expenditure arises depending on the type and construction of the detection system used, for minimising signal noise, it is not possible to eliminate signal noise entirely. Therefore, qualitative and quantitative evaluation of measured fluorescence signals continues to necessitate referencing or calibration of the experiments and the detection devices by means of fluorescence calibration standards. Calibration of detection systems by means of fluorescence calibration standards is carried out, inter alia, in order to be able to make statements regarding the sensitivity of the spatial and temporal resolution and the geometric image aberrations, such as e.g. the curvature of field of the respective system.

Calibration of detection devices regarding their temporal resolution is necessary because, for the purpose of differentiating between the actual fluorescence signal (which is often long-lived) and autofluorescence signals (which are often short-lived), measuring of the signals has to be carried out across an extensive time period.

When using CCD detectors, it is necessary, by means of standards, e.g. to determine the linearity and sensitivity of the detector in the fluorescence wavelength range used, the spatial and temporal resolution, as well as the curvature of field (flat field determination) of the detector. Confocal detection systems require calibration with regard to the regions which are excited, or which contribute to the overall intensity.

Calibration of experiments by means of fluorescence calibration standards is necessary because the fluorophores which are used as markers are subjected to considerable fluctuations with regard to their fluorescence yields, due to the environmental conditions to which they are exposed (e.g. autofluorescence of solvent components, pH value, temperature, irradiation time), and thus absolute quantification e.g. of hybridisation yields on probe arrays is only possible with some reservations.

Calibration of various fluorescence detection systems by means of fluorescence calibration standards is also very important because only such calibration permits a comparison of fluorescence signals obtained in experiments, which fluorescence signals were obtained using different detection systems and different devices within a system (comparison above system level or above device level).

In the state of the art, various teachings are known which are intended to make it possible to calibrate fluorescence detection systems or fluorescence signals.

For the purpose of calibrating fluorescence detection devices, it is e.g. possible to use chips which comprise a fluorescent plastic layer. Such calibration standards are associated with the disadvantage that they do not allow calibration of the detection systems with regard to their spatial resolution or with regard to their dynamic characteristics across a wide fluorescence range. Similarly, determining the curvature of field e.g. of CCD detectors is not possible with these standards, because, due to the thickness of the chip, homogenisation of the fluorescence signal through the chip occurs. Thus, calibration of the influence which the geometric relationships have on the detection of fluorescence signals (influence which in particular in the case of different detection systems and principles can assume a decisive role), cannot be undertaken, either above device level or above system level.

When using CCD-based fluorescence detectors and in particular when carrying out excitation by funnel-shaped or beam-shaped lasers or multispectral illumination systems such as e.g. cold-light sources, alignment of the illumination homogeneity with the use e.g. of movable diffusing disks requires expensive calculation and image manipulation to define the flat field. From the state of the art, no fluorescence calibration standards are known which make it possible to define the flatfield for correcting the illumination homogeneity in such direct-imaging systems.

Furthermore, there are fluorescence calibration standards which are based on doped glass. These standards, too, are associated with a disadvantage in that they do not permit calibration of the detection systems with regard to their spatial resolution or with regard to their geometric characteristics, because, due to the dimensions of such standards, homogenisation of the signals takes place as a result of the volume of glass. Confocal systems in which only certain regions and layers along the optical axis are excited, or contribute to the overall intensity, and in which the problem of transmission losses through the structural layers which are lying above exists, also cannot be calibrated with regard to their geometric characteristics if such standards are used.

WO 01/06227 describes the manufacture of a fluorescence calibration standard based on microparticles or nanoparticles, and further describes their application, both for calibrating fluorescence detection systems and for referencing fluorescence intensity signals in fluorometric assays. These standards are also not suitable for calibrating the fluorescence detection systems with regard to their spatial resolution. Thus, any comparison above the device level in the case of signal intensity data obtained from experiments based on probe arrays is only possible with some reservations.

In order to be able to differentiate the short-lived background fluorescence (e.g. of autofluorescent solvent molecules) from the actual fluorescence signal, and in order to be able to reference the actual signal, long-term emitting marker substances can be used as a standard, with the signals of said marker substances being proven by time-resolved detection methods. Frequently, these marker substances are phosphorescent chelates of rare-earth metals (in particular those of europium or terpium). However, these substances are associated with a disadvantage in that they can only be excited with UV light sources. Furthermore, the chelates used are often unstable in aqueous form.

In order to achieve quantitative evaluation of molecular interactions in probe-array-based experiments by means of fluorescence measurements, and in order to achieve standardisation of such signals, for the purpose of calibrating or referencing, the experiments are carried out by dual-colouring of the probe molecules, e.g. by competitive hybridisation (M. Shena, D. Shalon, R. W. Davis, P. O. Brown, Quantitative monitoring of gene expression patterns with a complementary DNA microarray, Science, 1995, 220,467-70, and D. Shalon, S. J. Smith, P. O. Brown, A DNA microarray system for analyzing complex DNA samples using two-color fluorescent probe for hybridization, Genome Res., 1996, 6, 639-45). Since in such calibration standards the signals obtained by way of the reference molecules always depend on the concrete experimental conditions, it is difficult to carry out a quantitative comparison above the device level or above the system level.

The disadvantages of the fluorescence calibration standards known from the state of the art clearly show that there is a considerable requirement for devices which make it possible to calibrate fluorescence detection systems with regard to their spatial and temporal resolution, as well as with regard to their geometric and dynamic characteristics.

In addition, there is a considerable requirement for devices for referencing fluorescence signals which make possible comparisons above system level and above device level and/or comparison above the level of individual tests, of fluorescence signals e.g. of experiments based on probe arrays.

SUMMARY OF CERTAIN INVENTIVE EMBODIMENTS

It is thus the object of the present invention to provide devices which make possible referencing of fluorescence signals with regard to the measured intensity and/or calibration of fluorescence detection systems with regard to their sensitivity, their spatial and temporal resolution, and/or with regard to their geometric and dynamic characteristics. It is a further object of the present invention to provide devices which easily make possible a comparison above device level and above system level, of fluorescence signals from experiments, which may e.g. be experiments based on probe arrays. Furthermore, it is an object of the present invention to provide fluorescence calibration standards which make possible comparison of fluorescence signal data above the level of individual tests. Moreover, it is an object of the present invention to provide devices which make possible referencing or standardisation of fluorescence signals taking into account bleach quenching effects and fluorescence quenching effects.

It is a further object of the present invention, to provide methods for producing such fluorescence calibration standards.

The characteristics of the independent claim serve to meet these and other objects which are set out in the description of the invention. Advantageous embodiments of the invention are defined in the dependent claims.

DETAILED DESCRIPTION OF CERTAIN INVENTIVE EMBODIMENTS

Figure 1:
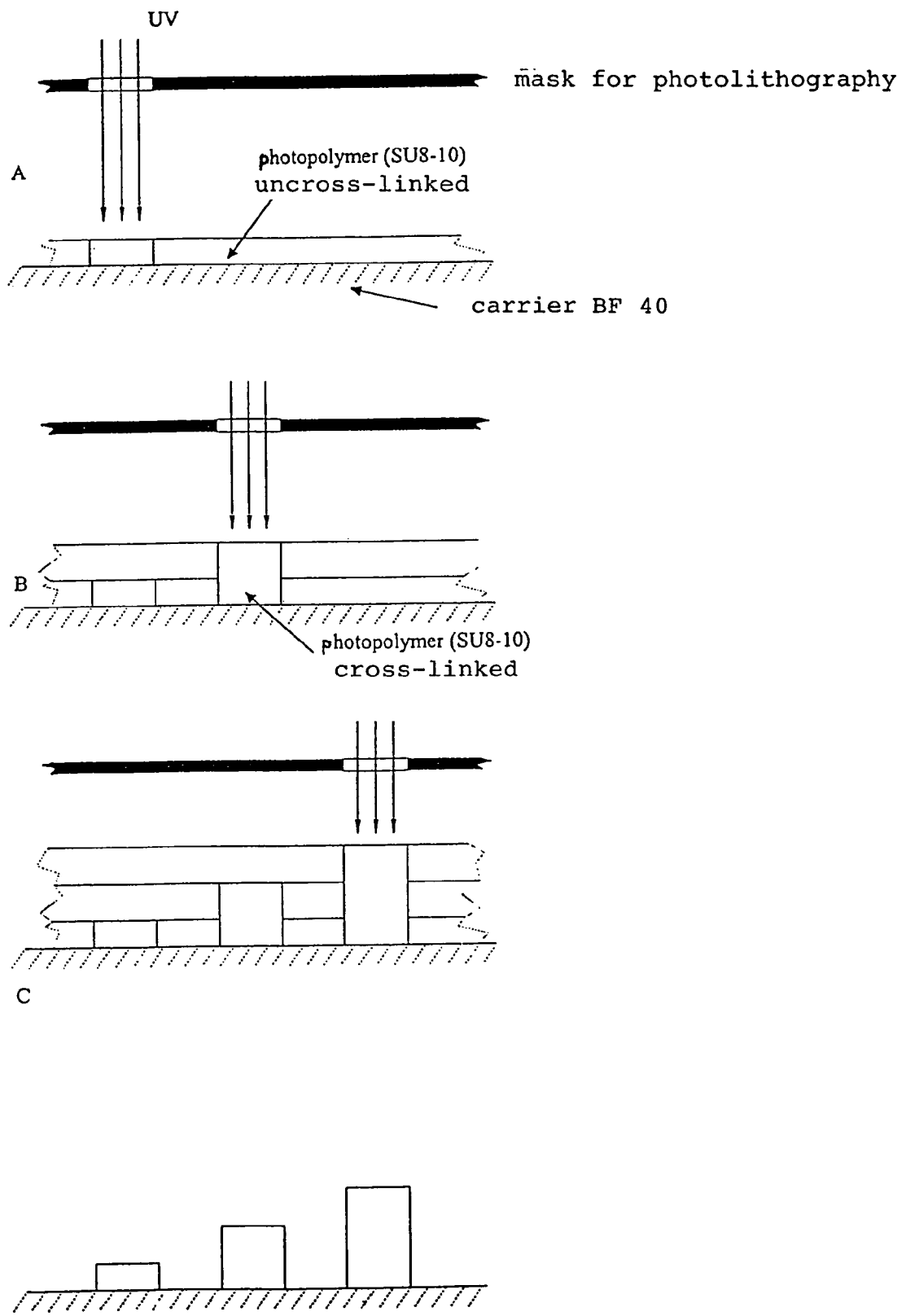
FIG. 1A is a side-view illustration of a first stage in the photolithographic production of a fluorescence calibration standard by way of multistage photolithography.
FIG. 1B is a side-view illustration of a second stage in the photolithographic production of a fluorescence calibration standard by way of multistage photolithography.
FIG. 1C is a side-view illustration of a third stage in the photolithographic production of a fluorescence calibration standard by way of multistage photolithography.
FIG. 1D is a side-view illustration of a fourth stage in the photolithographic production of a fluorescence calibration standard by way of multistage photolithography.

According to the invention, the objects are met in that at least one polymer layer is applied to defined regions of an essentially non-fluorescent carrier, such that these regions fluoresce after corresponding irradiation, wherein some of the applied polymer layers differ with regard to their thickness and/or composition.

After corresponding irradiation, the defined regions of such devices according to the invention, which devices hereinafter are also referred to as fluorescence calibration standards or standards, display a fluorescence whose intensity is predeterminably and reproducibly settable. Thus, fluorescence calibration standards according to the invention can be used for calibrating different fluorescence detection systems with regard to their spatial and temporal resolution, with regard to their geometric and dynamic characteristics, as well as with regard to their sensitivity.

Since the wavelength range of the fluorescence which after corresponding irradiation is produced in the defined regions of a fluorescence calibration standard according to the invention can predeterminably and reproducibly be set by changing the composition of the polymer layers, the fluorescence calibration standards according to the invention can be used for calibrating different fluorescence detection systems with regard to their dynamic characteristics.

The polymer layers of devices according to the invention are applied in defined areas whose form and size can predeterminably and reproducibly be set. Such fluorescence calibration standards, which are also referred to as structured fluorescence calibration standards, can be used for calibrating different fluorescence detection systems with regard to their spatial resolution.

Since the fluorescence characteristics of the fluorescence calibration standards according to the invention only depend on the thickness and/or the composition of the polymer layers applied in the defined regions, and e.g. are not affected by components of the target solutions, the fluorescence calibration standards according to the invention are suitable for evaluating and referencing, above the device level or detection level and/or above the level of individual tests, fluorescence signals which are measured e.g. in probe-array-based experiments.

The polymer layers which are applied to the defined regions of devices according to the invention can be one or several polymer layers which differ in their composition and/or thickness. The polymer layers comprise at least one fluorescent polymer or a polymer mixture, wherein at least one polymer component of the mixture is fluorescent. Preferred fluorescent polymers include e.g. positive photosensitive coatings and/or negative photosensitive coatings based on epoxy resins such as e.g. SU8 and novolak resins and/or PMMA and/or photosensitive polyimide and/or benzocyclobutene. Polymers which are suitable for the production of fluorescence calibration standards according to the invention, i.e. polymers which display fluorescence after corresponding irradiation, are also known from U.S. Pat. Nos. 6,091,488 and 4,482,424.

Apart from at least one polymer, the polymer layers of devices according to the invention can additionally contain fluorescent substances which are not polymers. Since these substances are embedded in the polymer layers, their fluorescence characteristics are not affected by environmental factors (e.g. components of the target solutions). Preferably, such fluorescent substances include chromophores, organic dyes such as e.g. azo dyes, triphenylmethane dyes, porphynine dyes and/or inorganic dyes such as e.g. metallic dyes and in particular lanthanides. Such substances also include perylene derivatives as mentioned in H. Langhals, J. Karolin, L. B.-A. Johansson, Spectroscopic properties of new and convenient standards for measuring fluorescence quantum yields, J. Chem. Soc., Faraday Trans., 1998, 94, 2919-2922, and S. Kalinin, M. Speckbacher, H. Langhals, L. B.-A. Johansson, A new and versatile fluorescence standard for quantum yield determination, Phys. Chem. Chem. Phys., 2001, 3, 172-174. In particular, these can include N,N'-bis (1-hexylheptyl)-3,4:9,10-perylenbis(dicarboximide), perylene-3,4,9,10-tetracarboxyltetramethylester, perylene-3,4,9,10-tetracarboxyltetrasodium salt and $N^2,N^3$-[bis(1-hexylheptyl)-benzo[ghi]perylene-2,3,8,9,11,12-hexacarboxyl-2,3:8,9:11,12-tris(dicarboximide)-$N^1,N^{1'}$-(1,2-ethyl)-[$N^{2'}$-(1-octylnonyl)-perylene-3,4:9,10-bis (dicarboximide).

In the devices according to the invention, the wavelength range of the fluorescence, which fluorescence occurs in the defined regions after corresponding irradiation, can be set by selecting the composition of the polymer layers. In a preferred embodiment of the invention, the polymer layers which have been applied in defined regions to a non-fluorescent carrier are characterised by inherent fluorescence occurring across a broad band, so that said polymer layers, after narrow-band excitation, display fluorescence signals in a wavelength range of major excitation, in the visible spectral range as well as in the near IR and UV ranges. In another preferred embodiment of the invention, the polymer layers display narrow-band inherent fluorescence in the defined regions, with the wavelength range of said inherent fluorescence depending on the composition of the polymer layers.

In a preferred embodiment of the invention, the polymer layers comprise only one polymer, so that the wavelength range of the fluorescence only depends on this polymer. In further preferred embodiments of the invention, the polymer layers comprise one or several non-fluorescent polymers and/or one or several additional fluorescent substances, so that the wavelength range of the fluorescence of these devices according to the invention depends on the type and the combination of the polymers and/or of the fluorescent substances.

According to the invention, the intensity of the fluorescence which is caused by a polymer layer in a defined region after corresponding irradiation can be set so as to be predeterminable in various ways. According to the invention, the intensity of the fluorescence caused in the defined regions after corresponding irradiation can be set by the composition of the polymer layers and/or the thickness of the polymer layers. According to the invention, the term "thickness of a polymer layer in a defined region" refers both to the thickness of the individual polymer layers in a region if several polymer layers have been applied in one region, and to the thickness which results from the sum of the thicknesses of the individual polymer layers in one area.

In a preferred embodiment of the invention, the setting of the intensity in a defined region takes place by successive application of polymer layers of uniform composition in this region. The polymer layer which arises in this region is of uniform composition. Accordingly, fluorescence calibration standards according to the invention can be produced which in all defined regions carry polymer layers of uniform composition but of different layer thickness. In a particularly preferred embodiment of the invention, in this way, fluorescence calibration standards can be produced in which the intensity of the fluorescence caused in a region after corresponding irradiation is proportional to the thickness of the polymer layer which has been applied in the corresponding region.

The intensity of fluorescence in the defined regions of calibration standards according to the invention can also be set by changing the composition of the polymer layers. According to the invention, the term "composition of the polymer layers" refers to the type and number of the polymer components in a polymer layer and/or of the additional fluorescent substances as well as the quantity of the polymer components and/or of additional fluorescent substances per unit area.

In a preferred embodiment of the invention, polymer layers of uniform thickness are applied in various defined regions, wherein the polymer layers differ only with regard to the quantity of the additional fluorescent particles per unit area. In this way, fluorescence calibration standards according to the invention can be produced, in which standards the intensity of the fluorescence caused in the regions after corresponding irradiation is proportional to the quantity of fluorescent particles in the various regions defined, if the layer thickness is the same. In another preferred embodiment of the invention, thus if the concentration of fluorescent particles in the polymer is constant, by changing the layer thickness, the resulting intensity can be set in a quasi-linear way.

A further option for setting the intensity of fluorescence calibration standards produced according to the invention consists of subjecting the polymer layers according to the invention to physical treatment methods such as irradiation and temperature treatment (tempering) during the manufacturing process. Without wishing to be tied to a hypothesis, there is presently an assumption that the degree of linkage or cross-linkage of the polymer layers, and correspondingly the fluorescence characteristics of the polymer layers, are changed by means of these treatment methods. The average person skilled in the art is familiar with the term "degree of linkage" or "degree of cross-linkage". In particular, polymers comprising duroplastic cross-linkage, e.g. the above-mentioned photosensitive coatings such as SU8, are suitable for setting the intensity of polymer layers by means of methods for altering the degree of cross-linkage.

According to the invention, by gradually applying polymer layers of different thickness and/or different composition and/or different degree of cross-linkage to several defined regions on the same carrier, fluorescence calibration standards can be produced which differ by a large bandwidth both with regard to the intensity and with regard to the wavelength regions of the fluorescence occurring after corresponding irradiation. Such fluorescence calibration standards according to the invention can be used in many applications for calibrating fluorescence detection systems with regard to their spatial and temporal resolution as well as to their dynamic and geometric characteristics. Such devices according to the invention can also be used as fluorescence calibration standards which easily make possible a comparison of fluorescence signals among different detection systems, and also among devices within a system.

Due to the chemical and physical characteristics of the polymers used and of additional fluorescent substances, the fluorescence characteristics, such as e.g. the quantum yield of the fluorescent regions, are subject to changes throughout the irradiation period. Consequently, the resulting intensity is reduced after a certain period of use (for bleaching compare also Miehler, 1992, "Kunststoff-Mikromechanik: Morphologie, Deformations-und Bruchmechanismen", Hanser, Munich/Vienna).

According to the invention, by means of suitable production protocols (e.g. by so-called tempering protocols), the polymer layers deposited in defined regions can be optimised with regard to their change in intensity over time, such that these changes are linear and therefore the intensity relationships of the resulting fluorescence in the individual defined regions of the structured standard remain constant.

Such fluorescence calibration standards according to the invention can be used for calibrating fluorescence detection devices with regard to their temporal resolution and for standardising experiments with regard to their progression over time. Since in such fluorescence calibration standards according to the invention the changes in intensity over time are linear, these standards can also be used for standardising experiments on detection devices whose optical characteristics are subjected to change over time (e.g. laser output or lamp output).

As preferred embodiments, fluorescence calibration standards according to the invention can thus be produced, whose fluorescence yield can be described as being linear or adequately predeterminable over the irradiation period and the ageing process. Such fluorescence calibration standards can e.g. be used for referencing fluorescence signals of experiments which were carried out at different points in time. Furthermore, said calibration standards make possible comparison of fluorescence signals above device level and above system level.

In a preferred embodiment of the invention, the polymer layers are applied in defined regions of different form and/or size on a carrier which essentially is non-fluorescent. In particularly preferred embodiments, these defined regions are of square, rectangular and/or circular shape, with the length of their sides or with their diameters ranging from 500 nm to 5 mm.

Such structured fluorescence calibration standards according to the invention can be used for calibrating different fluorescence detection systems with regard to their spatial resolution. In the context of the invention, the term "spatial resolution" refers to the separability of two imaged fluorescent points.

Since fluorescence calibration standards according to the invention can be produced whose defined regions comprise dimensional tolerances in the 10 nm range, such fluorescence calibration standards can be used in microscopic techniques such as e.g. in confocal 3-D microscopy as a standardisation instrument for lateral and axial distances.

In a particularly preferred embodiment, the defined regions have been applied in array-form to the carrier, i.e. several defined regions of the same size and shape have been grouped to form an array element, whereas regions of other shape and/or size have been grouped to form other array elements.

In preferred embodiments of the fluorescence calibration standards according to the invention, the thickness of the polymer layers can be set such that the maximum thickness of the different polymer layers in a region is significantly smaller than the minimal focal depth of commercially available confocal detection systems. According to the invention, the preferred layer thickness of such fluorescence calibration standards should be between a few nanometres and max. 50 micrometres, preferably the layer thickness should be between a few nm and 20 µm, between 100 nm and 10 µm, particularly preferably between 200 nm and 5 µm. According to the invention, the term "focal depth" refers to the region along the optical axis, in which region detection of fluorescence signals is possible. In conventional microscopy, this region is determined by the numeric aperture, while in confocal scanning microscopy this region is determined by the size of the pinholes. Such fluorescence calibration standards according to the invention can be used for calibrating physical structures and devices, for acquiring fluorescence signals, and for referencing fluorescence signals of correspondingly marked substances and substance groups.

According to the invention, the polymer layers are applied to essentially non-fluorescent carriers, preferably to carriers with optical transmittance. In preferred embodiments of the device, these carriers comprise glass, particularly preferred quartz glass and borofloat glass or non-fluorescent polymeric plates with optical transmittance, particularly preferred said carriers comprise polycarbonate, PMMA and/or films. In certain circumstances, materials without optical transmittance, which materials essentially comprise no inherent fluorescence, may also be suitable carriers.

In a preferred embodiment of the invention, the fluorescence calibration standards are connected to further carrier systems. These carrier systems also comprise essentially non-fluorescent materials. Preferably, they are materials with optical transmittance, such as glass, particularly preferably quartz glass, but also materials without optical transmittance such as plastic and/or metal, which materials essentially comprise no inherent fluorescence.

In a particularly preferred embodiment, this carrier system is a commercially available microscope slide, as used e.g. in immunofluorescence microscopy. It is possible e.g. to immobilise cells or tissue slices on such carriers and to evaluate them directly by aligning the signals with the fluorescence calibration standard according to the invention.

Integration of the fluorescence calibration standards according to the invention can e.g also take place directly on the carriers on which substance libraries are, or will be, deposited in the form of a probe array. Such fluorescence calibration standards make possible immediate referencing of fluorescence signals, thus making it possible to evaluate test-specific investigations. For the purpose of tying-in the substance libraries, the surface of the carriers can be functionalised, in at least the regions which are to contain the substance library, by the following groups: amino, carboxyl, aldehyde or epoxy groups. Further functional groups for tying substance libraries are known to the person skilled in the art.

According to the invention, the carriers on which the fluorescence calibration standards or the substance libraries are deposited in the form of probe arrays should be selected such that they essentially are non-fluorescent and, if necessary, provide optical transmittance. Preferred materials for the production of such carriers are glass, particularly preferred quartz glass, borofloat glass and/or polymers and/or silicon. It is also possible to select materials which do not provide optical transmittance but which are essentially non-fluorescent.

For integrating the fluorescence calibration standards according to the invention in probe arrays, these probe arrays can be functionalised by way of substance libraries on the basis of proteins, peptides or nucleic acids. Preferably, the protein substance libraries with which the fluorescence calibration standards according to the invention have been functionalised, are antibody libraries, receptor libraries, receptor-ligand libraries and/or hormone libraries.

Usually, the peptide libraries with which the fluorescence calibration standards are functionalised according to the invention are pharmaceutically or biologically active peptides, antigen libraries and/or receptor-ligand libraries and/or hormone libraries.

The nucleic acid libraries with which the fluorescence calibration standards are functionalised according to the invention preferably are DNA molecule libraries and/or RNA molecule libraries. Particularly preferred are mRNA libraries, rRNA libraries, genomic DNA libraries and/or cDNA libraries and/or plasmids.

In a preferred embodiment, fluorescence calibration standards according to the invention can be integrated directly in the fluorescence detection systems so that online calibration of the devices becomes possible. Since the characteristics of the fluorescence calibration standards according to the invention are predeterminably settable by way of the production process and by way of the composition and thickness of the polymer layer, as well as by way of the size and shape of the defined regions in which the polymer layers which fluoresce after corresponding irradiation, the fluorescence intensities of probe-array-based experiments, which intensities have been measured with different detection systems, can directly be compared with each other above system level and above device level.

The fluorescence calibration standards according to the invention can also be used as an external tool in order to calibrate several different detection systems in the manner described.

Fluorescence calibration standards according to the invention can also be integrated in closed chamber systems (e.g. PCR chambers and/or hybridisation chambers).

Fluorescence calibration standards according to the invention can be produced according to methods in which the layers which fluoresce after irradiation, are applied in defined regions to carriers according to the invention in a targeted way. Such methods are e.g. known from semiconductor technology (U.S. Pat. No. 6,091,488). The polymer layers of fluorescence calibration standards according to the invention can preferably be applied to the carrier by way of photolithographic methods, spotting, dry etching, ion implantation, printing-technology methods, rolling, injection moulding, or surface embossing.

Generally speaking, the polymer layers according to the invention, which are also referred to as functional polymer layers or functional layers, can be applied to the carrier by way of chemical and/or physical methods of coating. In the case of chemical methods, the application of the polymer layers can take place from the gas phase (e.g. by way of CVD or oxidation), from the liquid phase (e.g. by way of electrolytic, electrochemical or other wet chemical methods) or from the solid phase (e.g. by way of oxidation). In the case of physical methods, the application can take place from the gas phase or from the plasma (e.g. by way of PVD, sputtering or vapour-depositing), from the liquid phase (e.g. by way of spin-on methods, painting, spraying or immersion) or from the solid phase (e.g. by way of lamination). Combinations of these methods, or subsequent modifications such as ion implantation may also be applied (e.g. PECVD). The respective methods and corresponding embodiments are known to the person skilled in the art (see e.g. W. Menz, J. Mohr, "Mikrosystemtechnik für Ingenieure", VCH, 1997).

The polymer layers according to the invention can be structured by means of various methods which are known to the average person skilled in the art. These can be biochemical methods, e.g. the enzymatically arranged selective structuring (described in WO 98/08086) or chemical and/or microtechnical methods. These include selective etching of the functional layer against a masking arrangement which is insensitive even to the etchant (e.g. liquid etching or dry etching). Also applicable are methods which cause selective changes in characteristics by means of irradiation, e.g. by irradiation using UV or lasers. This includes photolithography. Other methods include self-assembling layers. These methods can be carried out with the use of masking, or by "direct-writing" devices (spotting). Print-technology methods such as spotting or offset printing or other methods such as rolling, stamping, injection moulding or surface embossing methods can also be applied. Various embodiments of the methods are known to the average person skilled in the art (see e.g. W. Menz, J. Mohr, "Mikrosystemtechnik für Ingenieure", VCH, 1997).

In a preferred embodiment, the polymer layers are applied by negative or positive photolithographic methods, with particular preference by way of negative photolithographic methods. Particularly preferred are negative photolithographic methods in which the polymer layers become non-soluble after irradiation in the developing agent. In contrast, non-exposed regions remain soluble in the developing agent and can be removed. Such photolithographic methods for transferring the structure by means of a photoresist are known to the person skilled in the art. In this context, chemical and physical methods which make it possible to apply a homogeneous functional layer to the carrier are preferred. Particularly preferred methods include CVD, PVD and spin-on methods.

The parameters, the selection of which in the case of photolithographic methods (and also other methods) makes it possible to set the thickness of the polymer layers, comprise the treatment parameters (processing parameters) such as the circulation speed, the duration of the production process, the viscosity of the polymer, the temperature and/or the atmospheric humidity. If photopolymers are used, the treatment parameters also comprise the irradiation dose, the parameters of the development process, and the tempering process.

In the case of photolithographic methods, the form and size of the defined region in which the polymer layers are applied can be determined by using a mask and/or pinholes, e.g. by using a mask at a scale of 1:1. Depending on its recesses, the mask makes it possible according to the invention to set various geometric forms and sizes for the defined regions. According to this method, it is also possible to produce fluorescence calibration standards according to the invention, in which fluorescence calibration standards the polymer layers applied to various defined regions have an array form. Preferably structured chromium on glass and/or on quartz is used for pinholes.

By repeating the photolithographic process, fluorescence calibration standards according to the invention can be produced in which polymer layers with different composition and/or thickness have been applied in various regions. Moreover, by changing the tempering protocols and/or the irradiation protocols which are used in photolithographic methods, the degree of cross-linkage (and thus the intensity) of the polymer layers can be changed in a targeted way in defined regions. By changing the tempering protocols, it is also possible to set in a targeted way the bleaching behaviour of fluorescence calibration standards according to the invention.

In order to combine fluorescence calibration standards produced according to the invention e.g. with an essentially non-fluorescent carrier system with optical transmittance any process can be used which combines the calibration standard with the carrier system while not negatively affecting the characteristics of the fluorescence calibration standard. Installation requires that, by means of suitable methods and devices, the surface of the standards be aligned relative to the plane of sample carriers such that unambiguous allocation of the position of the fluorescent layers in height and position is possible in relation to defined regions of the carrier (e.g. outside edges). For example, temporary adhesion or vacuum devices are suitable for this purpose. Preferably, the fluorescence calibration standard is applied to the carrier system by way of adhesion, position adjustment, or a vacuum system.

When producing such fluorescence calibration standards according to the invention, care must be taken that the methods for assembling the fluorescence calibration standards and the probe arrays do not negatively affect the function of the components. Accordingly, it must be ensured that e.g. the adhesives used do not display any autofluorescence, and that no significant scattering or reflection occurs as a result of the components used.

If the fluorescence calibration standards e.g. are functionalised with substance libraries as probe arrays, the fluorescence calibration standard can be connected to the carrier system on which the substance libraries are located.

In another preferred embodiment, the fluorescence calibration standards on carriers can first be produced in the wafer scale, with the corresponding individual fluorescence calibration standards subsequently being functionalised by depositing substance libraries in array-form.

The fluorescence calibration standards according to the invention can be used in various ways for calibrating fluorescence detection systems. By using fluorescence calibration standards according to the invention for equipment-specific calibration, the equipment characteristics can be defined. For example, the respective shape and size of the defined regions in which the polymer layers are deposited, which polymer layers are fluorescent after corresponding irradiation, can be used to determine the spatial resolution. Fluorescence calibration standards according to the invention, which standards comprise polymer layers of different thickness but uniform composition in several defined geometric regions, as a result of which the intensity of the fluorescence caused by corresponding irradiation in the various regions is proportional to the polymer layer thickness, make it possible to calibrate a corresponding detection system with regard to its dynamic characteristics. According to the invention, the term "dynamic characteristics" refers to the region of evaluable fluorescence intensities during one reading. For example, in this way the intensity region can be determined in which a CCD detector is to work in a linear way. Such fluorescence calibration standards according to the invention can also be used for setting the sensitivity of the detection system, i.e. for determining what minimum or maximum fluorescence intensities a detection system will still consider to be a signal.

Fluorescence calibration standards according to the invention, in which standards the intensity of the fluorescence caused after corresponding irradiation in different geometric regions with polymer layers of different thickness and/or of different composition predeterminably and controllably decays, can be used to draw conclusions concerning equipment-specific bleaching of fluorescence signals.

Furthermore, fluorescence calibration standards according to the invention can be used for calibrating the geometric characteristics of detection systems, in particular for correcting the curvature of field (flat field determination) in the case of CCD detectors.

According to the invention, the term "geometric characteristics" generally refers to the local resolution, image scale, curvature of field and other geometric aberrations which result from the optical construction.

Since the fluorescence characteristics of fluorescence calibration standards according to the invention do not depend on external factors and can predeterminably and reproducibly be set, they can be used for calibrating different devices using the same detection principle (calibration above the device level) or for calibrating devices using different detection principles (calibration above the system level). Calibration can take place in relation to standard values which are e.g. used in workgroups and laboratories, with fluorescence signals from experimental measurements subsequently being related to said standard values.

In this way, the signals which are obtained, with different detection systems, during evaluation e.g. of a probe-array-based experiment, are directly comparable (comparison above the level of individual tests).

Fluorescence calibration standards according to the invention, which standards have a large bandwidth with regard to the wavelength and intensity of the fluorescence caused in the defined regions after irradiation of the polymer layers, can also be used for test-specific referencing of fluorescence signals. This is possible because the test-specific signals can e.g. be related to the fluorescence of a defined region, with the characteristics of said fluorescence being in the region of the test signal. In this way, standardisation of the test signals is possible. From the standardised experimental data obtained with the use of fluorescence calibration standards according to the invention, those errors which result from the use of different detectors or different settings of the detectors are significantly rectified. The data can thus be directly compared. Fluorescence calibration standards according to the invention thus make possible comparison of fluorescence signal intensities above the level of individual tests and above the device level, said intensities having been obtained during probe-array-based experiments and tests.

Normally, the settings of scanners are matched to the corresponding readings obtained. If in a probe-array-based experiment, the resulting fluorescence signal is weak, the laser output or the sensitivity of the detector (e.g. the bias voltage if a PMT system is used, or the integration time if a CCD system is used) is increased. Furthermore, the devices are subject to device-specific fluctuations. This is critical in particular if results from different time periods are to be compared, since, e.g. in the case of laser scanners, the output of the lasers used can change dramatically. Comparison of fluorescence intensity signals, which were measured during the same type of probe-array-based experiments but which were measured at different points in time, is possible without any problems with fluorescence calibration standards according to the invention (time-to-time comparison), since the device fluctuations due to age can be standardised by way of the bleaching behaviour of the standard. In this way, by means of fluorescence calibration standards according to the invention, detection systems can also be calibrated with regard to their ageing characteristics, such as e.g. change in the lamp output.

If the fluorescence signals which were measured during various probe-array-based experiments are to be compared with each other, as far as evaluation of the results is concerned, in particular the inhomogeneity of the biochemical and fluidic processes in the sample, and the difficulties associated with spot detection pose a significant problem during evaluation. These problems render the qualitative comparison of different probe arrays more difficult. Fluorescence calibration standards according to the invention make it possible to considerably limit the errors. Qualitative comparisons of results which were obtained while carrying out experiments using different probe arrays on the same device now become possible (test-to-test comparison).

Since the fluorescence calibration standards presented also make it possible to calibrate different detection systems, the results of probe-array-based experiments can be analysed above the device level and above the system level, and thus also above the laboratory level.

Devices which are characterised in that on an essentially non-fluorescent carrier in one or several defined regions, polymer layers have been applied, which with regard to their layer thickness and composition are uniform, can also be used for referencing fluorescence signals. Such devices are in particular suitable if they comprise several defined regions, for calibrating fluorescence detection systems, with regard to their spatial resolution, above the device level and above the system level.

According to the invention, the polymer layers of such devices can be of the same composition as mentioned above, i.e. they can comprise fluorescent polymers, polymer mixtures containing at least one fluorescent polymer, and/or additional fluorescent substances.

In these devices, the intensity and the wavelength range of the fluorescence caused in the regions after corresponding irradiation are predeterminably and reproducibly settable by selecting the composition of the polymer layers, by selecting the layer thickness, and by changing the degree of cross-linkage. Other characteristics, too, such as the bleaching behaviour, as well as the size and form of the defined regions, are settable in the manner described above. Likewise, such devices can be produced using any of the methods described above.

Such devices can generally be used for qualitative and quantitative referencing of fluorescence signals, and can be used with particular preference for referencing fluorescence signals obtained in probe-array-based tests and/or for calibrating fluorescence detection systems.

With particular preference, such devices can be used for calibrating fluorescence detection systems with regard to their spatial resolution. Since the polymer layers which have been applied to one or several defined regions are uniform with regard to their composition and layer thickness, they are not suitable for calibrating the dynamic characteristics of fluorescence detection systems. Nor is it possible to use these devices for calibrating detection systems by comparing the relationships between different intensities which occur after irradiation of different regions.

However, such devices can e.g. be used for aligning experimentally obtained fluorescence signal data to standard values, thus making possible comparison of fluorescence signals above device level and above system level. These devices also make it possible to calibrate fluorescence detection systems with regard to their sensitivity and their device-specific bleaching behaviour at the intensities and wavelength ranges determined by the composition and thickness of the polymer layers.

Below, examples are provided which represent particularly preferred embodiments or uses of fluorescence calibration standards according to the invention. The examples provided are not to be interpreted as being limiting in any way or manner.

EXAMPLE 1

Photolithographic Production of a Fluorescence Calibration Standard According to the Invention, in the Wafer Scale (FIG. 1)

The example shows how a universal fluorescence calibration standard according to the invention is produced on a polymer base with the use of negative photolithography. In this example, a fluorescence calibration standard according to the invention is produced, which standard in different regions of the same form and size comprises polymer layers of different thickness but essentially of identical composition. Thus, the intensities of the fluorescence, which is caused in the regions after corresponding irradiation, are proportional to the layer thickness.

Materials which in the desired fluorescence spectrum display high transparency and low inherent fluorescence were used as carriers. In the present case, borofloat glass from Schott (BF 40, diameter: 100 mm, thickness: 0.7 mm) was selected as a carrier material. In contrast, the actual functional material (i.e. the polymer layers) should display strong inherent fluorescence. In the embodiment selected, SU8-10, dissolved in PGMEA (organic solvent from Sigma), was selected as a polymer, because it meets the above-mentioned requirements. SU8-10 is a negative, epoxy-based photopolymer, which polymerises at UV irradiation below 365 nm (U.S. Pat. No. 4,882,245). Inherent fluorescence and photostructurability are associated with a considerable advantage in that the selected polymer can be structured by way of photolithographic processes.

At the beginning of the production process, the carrier material was tempered (180° C., 20 min). Consequently, any adsorbates (often $H_2O$) were removed, since they would prevent the SU8 polymer layer from adhering properly to the substrate. In order to enforce the positive effect, the surface of the substrate was modified with 3-glycydoxypropyltrimethoxysilane.

Subsequently, a first layer with a thickness corresponding to the desired fluorescence or the desired sensitivity was applied to the substrate (see FIG. 1). The spin-on process was used for this, wherein the desired thickness or the fluorescence was set by selecting the parameters (duration: 30 s, rotational speed: 5000 rpm, acceleration: 100 rpm/s for 10 s, and 1000 rpm/s for 20 s, degree of thinning with PGMEA). As a result of this, the polymer was homogenously distributed on the substrate, and the solvent was expelled. Subsequent tempering above the glass-transition temperature (95° C., 15 min, so-called pre-bake) formed and homogenised the layer.

Subsequently, the polymer layers were structured by means of the usual microphotolithography. To this purpose, by irradiation of the photopolymer with UV light (15 min at approx. 300-450 nm at 15 mW/cm$^2$, so-called exposure), its solubility in the developer (in this case PGMEA) was altered. SU8-10 displayed a density-step negative behaviour, i.e. the regions exposed to UV irradiation polymerise, while regions which were not exposed remained soluble in the developing agent. Irradiation took place by way of mask projection using lithography masks which comprised correspondingly thin chromium structures on quartz. This quartz mask had the desired lateral geometry of the standard, which geometry was imaged onto the polymer at a scale of 1:1. The smallest structures in the mask thus also determined the smallest structures of the standard or of the smallest resolution test on the standard, which resolution test is to be detected.

Subsequently, in a tempering step, cross-linkage of the exposed region was completed (95° C., 15 min, so-called post-exposure bake). At this stage, the unexposed regions still remained untouched by the developing agent. After this, the above-mentioned procedure (spin-on, pre-bake, exposure, post-exposure bake) was then repeated several times, wherein the previously irradiated (and thus cross-linked) regions remained unexposed to radiation in subsequent irradiation steps, by corresponding masks. In the example, photosensitive coating, exposure to irradiation, and tempering were carried out three times in succession (FIG. 1). In this process, the layers were composed as follows with regard to the polymer:

1st layer: SU8-10 (MicroChem Inc.) dissolved in PGMEA (Sigma) 50% w/w

2nd layer: SU8-10 (MicroChem Inc.) dissolved in PGMEA (Sigma) 33% w/w

3rd layer: SU8-10 (MicroChem Inc.) dissolved in PGMEA (Sigma) 20% w/w

The photopolymer SU8-10 was dissolved in PGMEA at various weight ratios. As a result of this, the viscosity of the solution differed, so that it was possible to produce polymer layers of various thickness. The solvent was later expelled to a very large extent (more than 95%), so that the composition of the polymer layers was essentially identical.

After this, the polymer structure was developed by immersion in PGMEA (Sigma) (120° C., 30 min, so-called hard bake). This resulted in step-shaped geometric structures (FIG. 1). The step heights then corresponded to a respective fluorescence intensity, while the lateral geometries corresponded to the resolution.

EXAMPLE 2

Examples of Fluorescence Calibration Standards According to the Invention

Figure 2A:
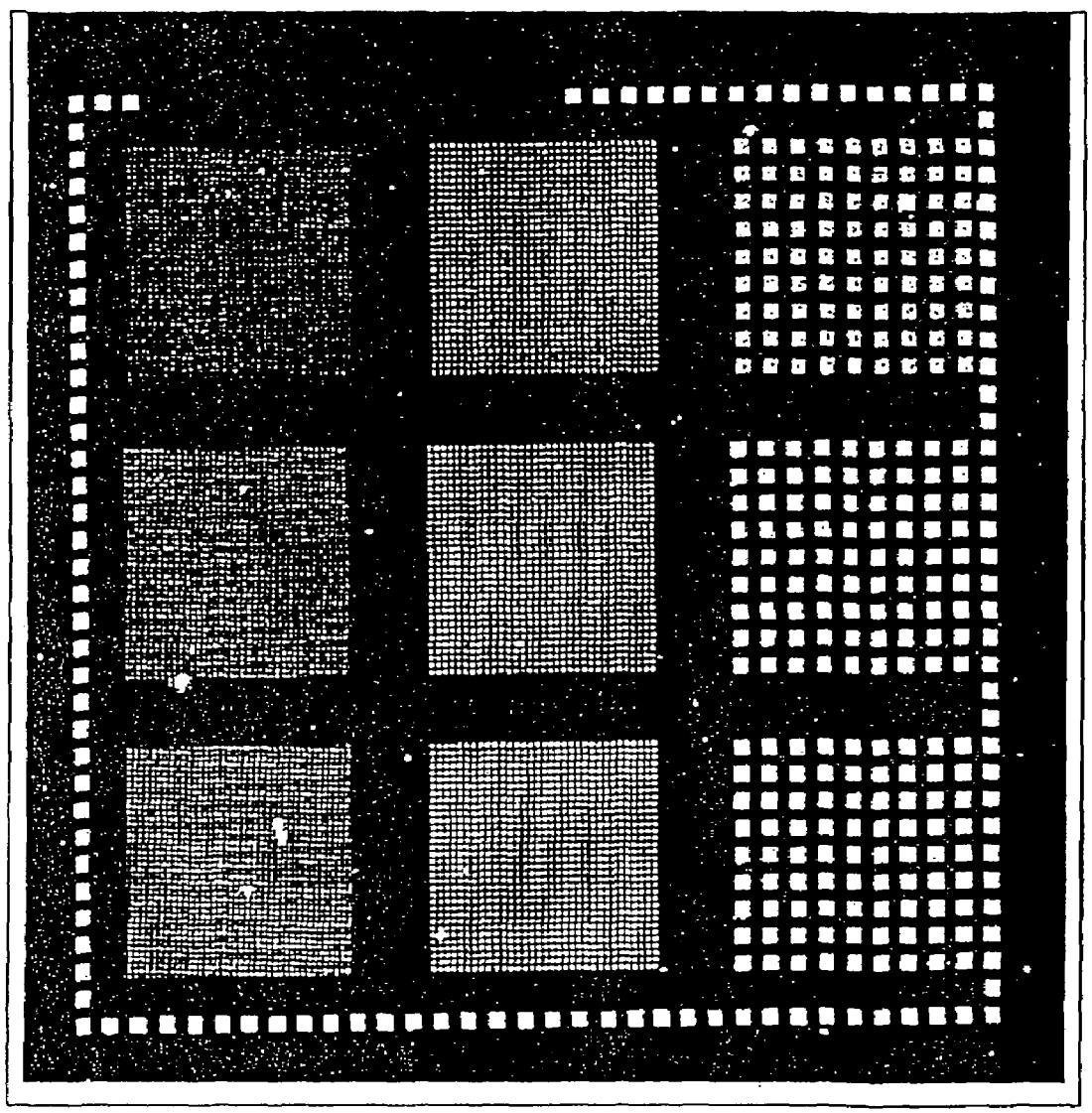
FIG. 2A is a top-view illustration of one embodiment of a fluorescence calibration standard in array-form, microlithographically produced on borofloat glass.

FIG. 2A shows a fluorescence calibration standard according to the invention, in array-form, microlithographically produced on borofloat glass (Schott) according to the method described in Example 1. The standard comprised 9 array elements, all comprising fluorescent polymer layers of square shape. The squares of the 9 array elements comprised 3 intensity stages which resulted from 3 different thicknesses. By way of different structural sizes and spacings, different integration densities of molecular arrays were simulated. The standards were generated in the wafer scale and were made into individual chips.

The standard is suitable for determining the spatial resolution, the geometric errors, the imaging optical and electromechanical and information-technology systems, and the sensitivity of the respective device at the time the reading was taken. In addition, the standard can be used for evaluation, above device level, of the fluorescence signals of probe-array-based experiments. To this effect, the described fluorescence standard was read out in various reader systems, was exported as 16 bit-*.tif images, and was analysed by means of special software (IconoClust by Clondiag). The fluorescent structures, of different size, on the fluorescence calibration standard can be used for correcting geometric deviations of the different detection systems. For example, using the disclosed fluorescence calibration standard, the curvature of field of an optical system for fluorescence detection can be analysed by means of suitable image processing methods. The curvature of field can then be eliminated by corresponding settings of the optical elements or information-technology elements.

Moreover, it is possible to attune the settings of the detection systems, e.g. with regard to the laser output or lamp output, the integration time for each spot/sub-array, or the signal amplification/setting of the detector, to a particular value of the resulting fluorescence of the standard. In this way it is possible, e.g. to determine long-term drift of a detection apparatus which can be caused by the aging process of the lasers, lamps or detectors used.

Different fluorescence systems can thus be calibrated by means of the fluorescence calibration standard with regard to their performance-determining parameters. Accordingly, the fluorescence signals which were measured during evaluation of a probe-array-based experiment, with the use of different detection systems, can directly be compared to each other.

Figure 2B:
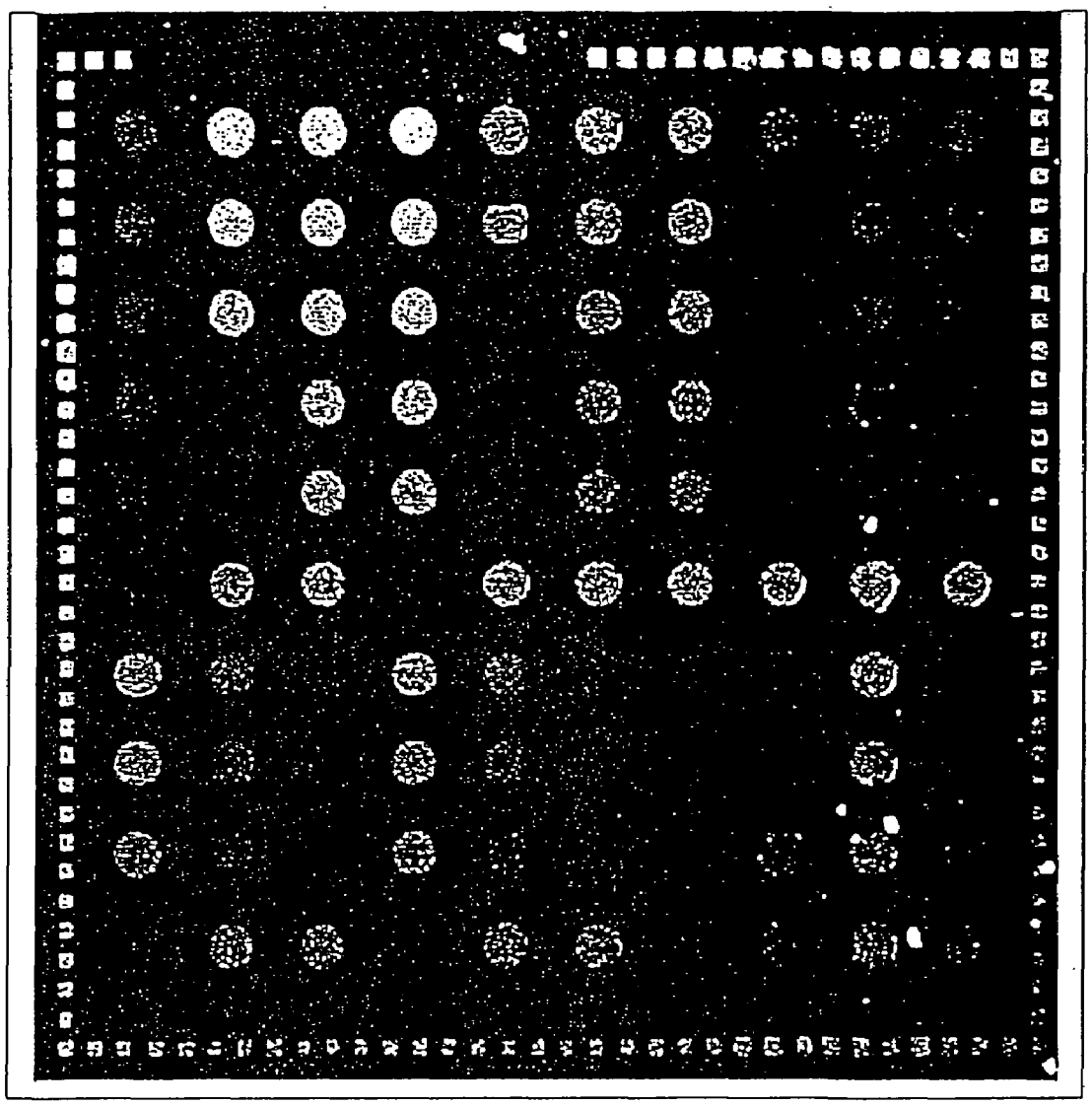
FIG. 2B is a top-view illustration of one embodiment of a fluorescence calibration standard in array form, produced by spotting on borofloat glass.

FIG. 2B shows a fluorescence calibration standard according to the invention, in array form, which was produced on borofloat glass (Schott) by spotting. First, fluorescent standards were produced on different carriers, by producing polymer mixtures SU8 (MCC Inc.) and novolak resin (AZ 1514 Clariant) at a mass ratio of 1:2, 1:3, 1:5, and applying them to the glass substrates. For this purpose, microscope slides were cleaned and by means of a pin spotter (Microgrid 2/Biorobotics) spotted with the polymer mixtures, with the use of a non-slotted spotter pin (Solid-pins/Biorobotics). As an alternative, the polymer mixtures were applied by means of a piezo-driven dispenser head (diameter 100 µm, heated nozzle of Microdrop). The dispenser nozzle was heated (55° C.).

Subsequently, the samples were treated as follows:
Pre-bake: 95° C., 15 min
Exposure: 1 min, 15 mW/cm², floodlighting
Post-bake: 95° C., 15 min
Hard-bake: 120° C., 60 min The standard produced in this way comprises circular regions (spots) of uniform dimension, with the polymer layers of said spots differing both with regard to their thickness and their composition. For this reason, the standard comprises a wide spectrum of intensities and wavelength ranges of the fluorescence which can be caused in the spots. The standard can be used in the way as that shown in FIG. 4A.

EXAMPLE 3

Integration of fluorescence calibration standards according to the invention in carrier systems.

Figure 3:
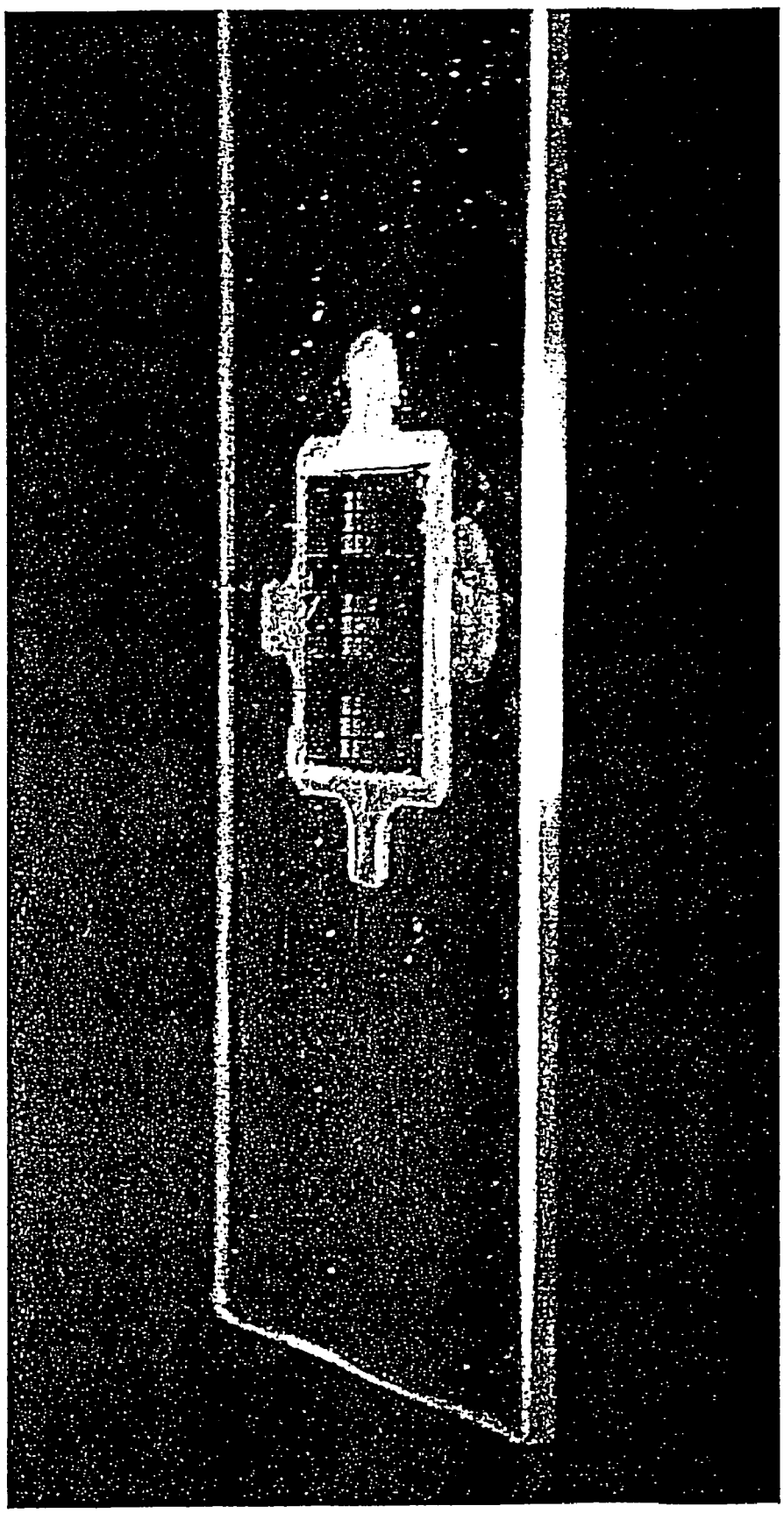
FIG. 3 is a perspective illustration of one embodiment of a fluorescence calibration standard attached to a microscope slide with adhesive.

FIG. 3 shows how a fluorescence calibration standard according to the invention has been applied to a microscope slide by way of adhesive. Polydimethyl siloxane (Sylgard® made by Dow) was used as an adhesive. Such standards can be used as an external tool for calibrating different detection systems.

EXAMPLE 4

Setting the intensity and the leaching behaviour in fluorescence calibration standards according to the invention—using fluorescence calibration standards according to the invention for a period covering several readings.

This example shows that in the case of microlithographic production of fluorescence calibration standards with polymer layers of three different thicknesses (d1, d2, d3), a tempering protocol can be selected such that there is a linear decay in the intensity of the fluorescence caused in the defined regions after multiple irradiation.

Figure 4A:
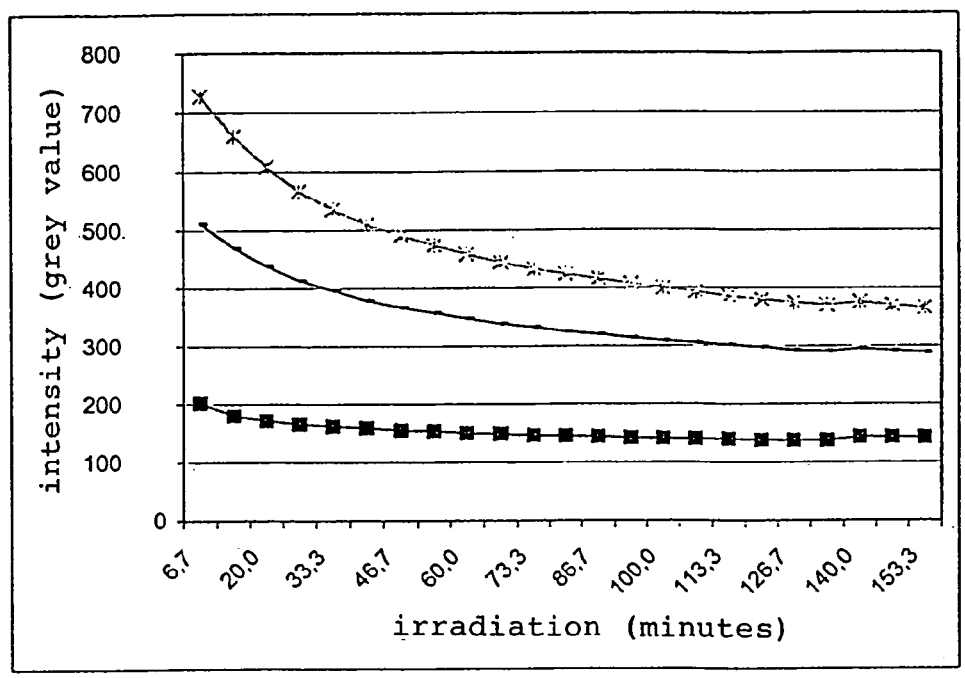
FIG. 4A is a graphical illustration of changes in the luminescence intensity as a result of the effect of irradiation in the visible range (bleaching) without thermal treatment, wherein the intensity is shown as a grey-scale value.
Figure 4B:
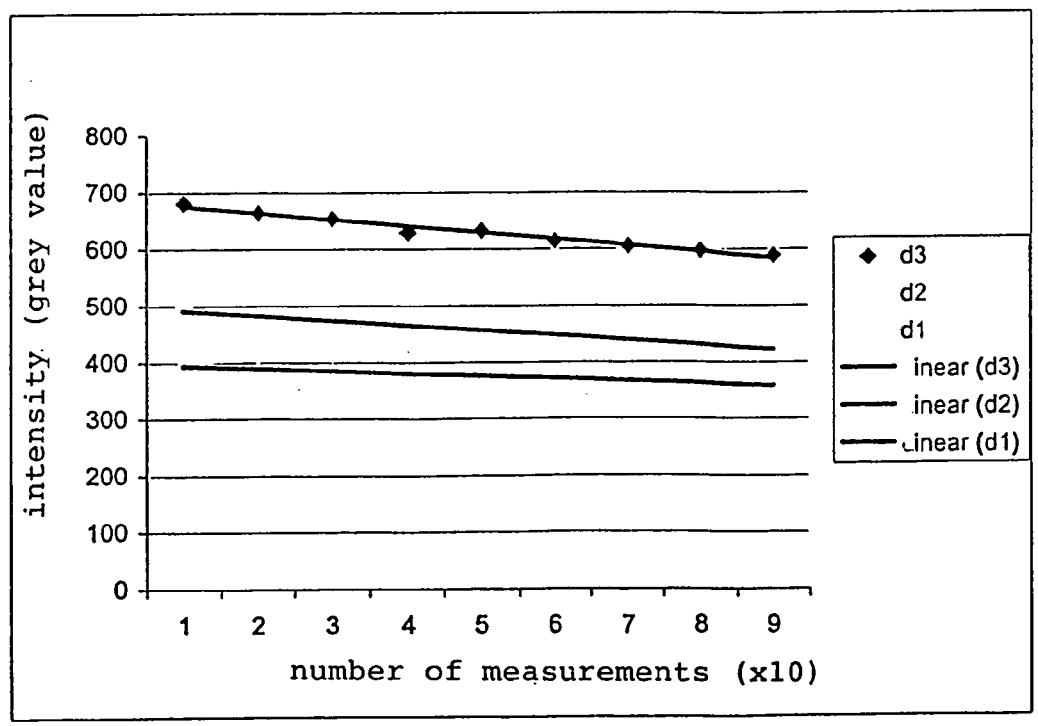
FIG. 4B is a graphical illustration of change in the fluorescence intensity over the number of measurements in a white-light/CCD system after performing a matched tempering protocol.

FIG. 4A shows the bleaching behaviour of the three layers without thermal treatment. The bleaching behaviour is non-linear. FIG. 4B shows the bleaching behaviour of the three layers after thermal treatment. The bleaching behaviour is linear. In order to linearise the progression over time of the change in the resulting fluorescence intensities, during the production process the probes were subjected to thermal treatment for two hours at 180° C. in the oven, before being irradiated at 40 mW/cm² for approx. 40 minutes at a wavelength ranging between 520 and 600 nm. In this process, the intensity behaviour changes to such an extent that the thickness ratio is no longer proportional to the resulting intensity ratio. However, the intensity ratios of the structures which differ in thickness are now constant during irradiation (see FIG. 4C).

It is shown that by changing the tempering protocol, fluorescence calibration standards can be produced whose bleaching behaviour is far less pronounced and far more constant. The readings were obtained using a confocal biochip-scanner Scanarray 4000 (Packard) at 100% laser output and 85% PMT gain.

Figure 4C:
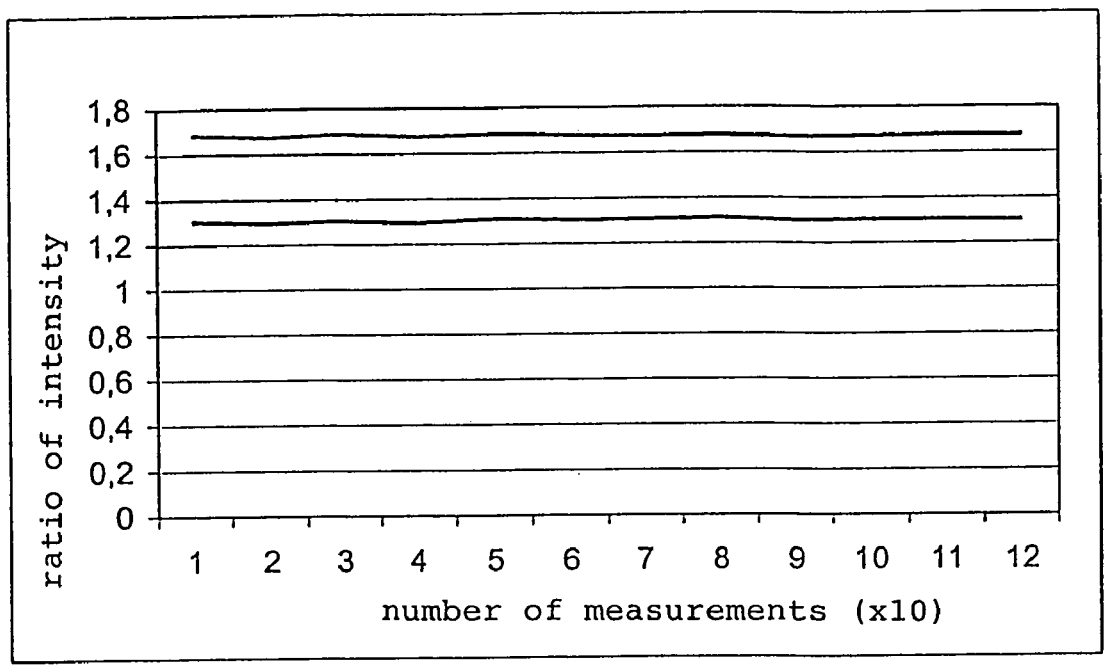
FIG. 4C is a graphical illustration of the intensity ratio as a function of the number of measurements in a white-light/CCd system with the use of matched tempering protocols, wherein the upper line shows the d3/d2 ratio, and the lower line shows the d2/d1 ratio from FIG. 4A.

Such long-term stable fluorescence calibration standards are outstandingly suited for calibrating fluorescence detection systems with regard to their characteristics caused by ageing, because the intensities of the three layer-thicknesses change to the same extent, and thus the ratio of the intensities of the layers whose thickness is different, remains constant (see FIG. 4C).

EXAMPLE 5

Referencing Fluorescence Signals

Fluorescence calibration standards as described in Example 1 were produced in which polymer layers of differing thickness were applied in the defined regions.

Figure 5:
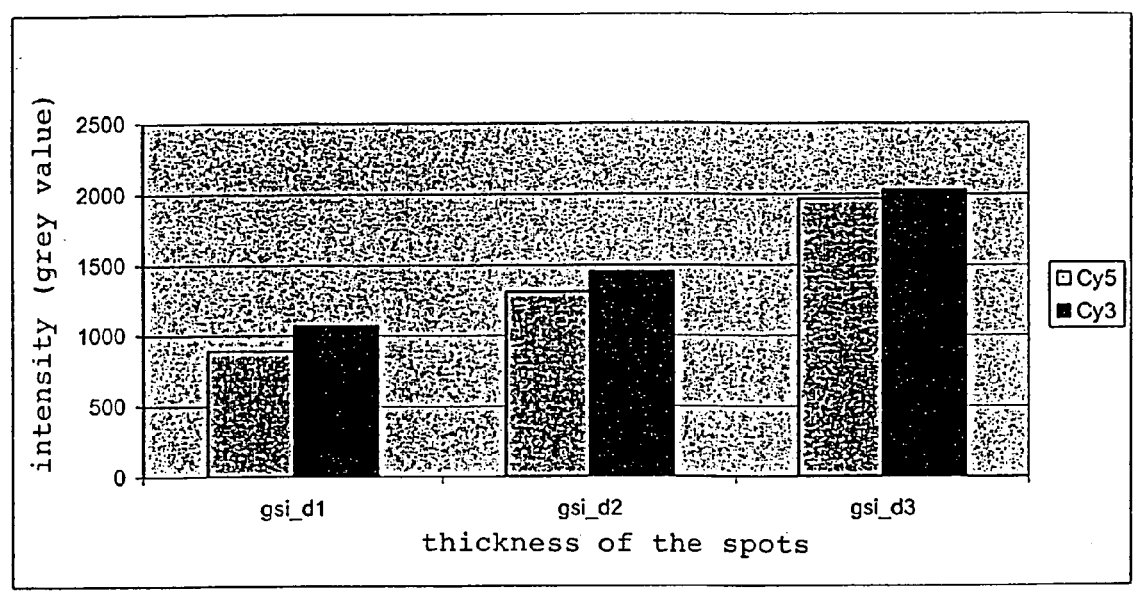
FIG. 5 is a graphical illustration of intensity as a function of spot thickness for a scan of various dyes.

FIG. 5 shows that with this standard, referencing of measurements in various wavelength ranges becomes possible (Cy3 and Cy5 absorb at different wavelengths) and that the measured intensities are proportional to the layer thickness (d1, d2, d3). Thus, due to its broadband fluorescence behaviour in different wavelength ranges, this fluorescence standard can be used for calibrating reader systems. Such fluorescence calibration standards which comprise inherent fluorescence across a broad band, also make it possible to reference fluorescence signals in various wavelength ranges. Furthermore, such standards make it possible to calibrate laser scanners with regard to their sensitivity. Readings were taken with a confocal biochip scanner Scanarray 4000 (Packard) at 100% laser output and 85% PMT gain.

EXAMPLE 6

Standardisation of probe-array-based experiments.

Figure 6A:
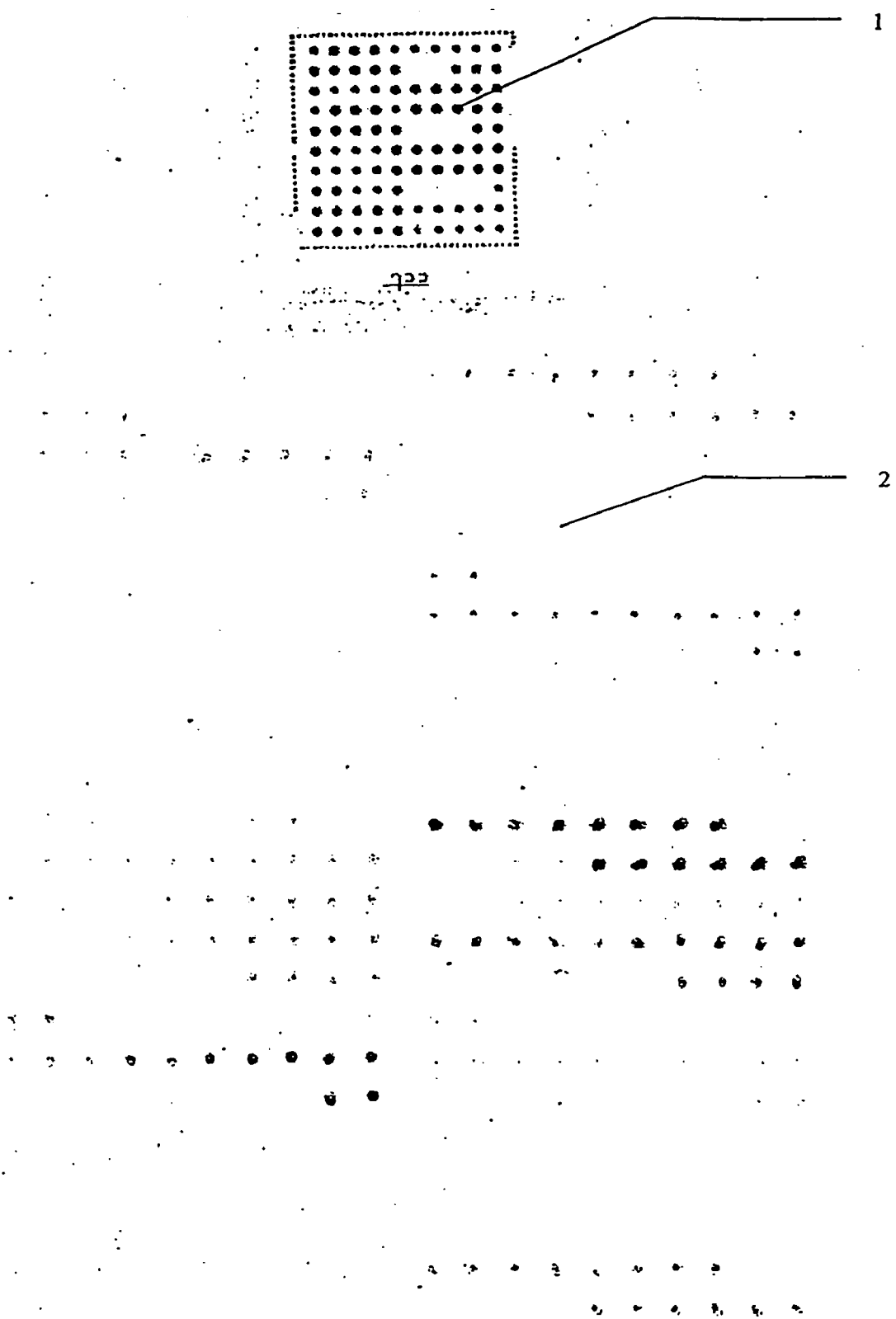
FIG. 6A is an inverse scan of a spotted probe array showing the fluorescence calibration standard (1) in the upper part, the probe array (2) below it for spotted PCR products after hybridization with cDNA marked with Cy3/Cy5.

For the standardisation of probe-array-based experiments, fluorescence calibration standards according to the invention were used which also comprised a probe array. In this way, the fluorescence calibration standard can then also be taken into account during the read-out procedure before or after the biochemical interaction reaction is carried out (see FIG. 6A).

Fluorescence calibration standards according to the invention were applied to epoxidated microscope slides (QMT) by means of ultrasonic drilling and adhesion, said standards comprising in the defined regions polymer layers of the same polymer thickness but with a different content with regard to the polymer components. Thus, after corresponding irradiation, the intensity of these regions differed. After this, a number of PCR products (aceA, acs, amiB, ampG, argC, atpA, creB, icda, napH, rpoA, rpoH, rpoS) were applied to the carrier by means of spotting (BioRobotics Microgrid II). Specially cleaned cDNA which was marked using fluorescence dyes (Cy3 or Cy5, Amersham) was immobilised on the PCR spots by hybridisation. Subsequently, the samples were read out by means of a confocal laser scanner (Affymetrix, Packard), and the results were analysed by means of special software (IconoClust by Clondiag). The results were evaluated by way of referencing to the different intensities of the various regions of the fluorescence calibration standard.

Figure 6B:
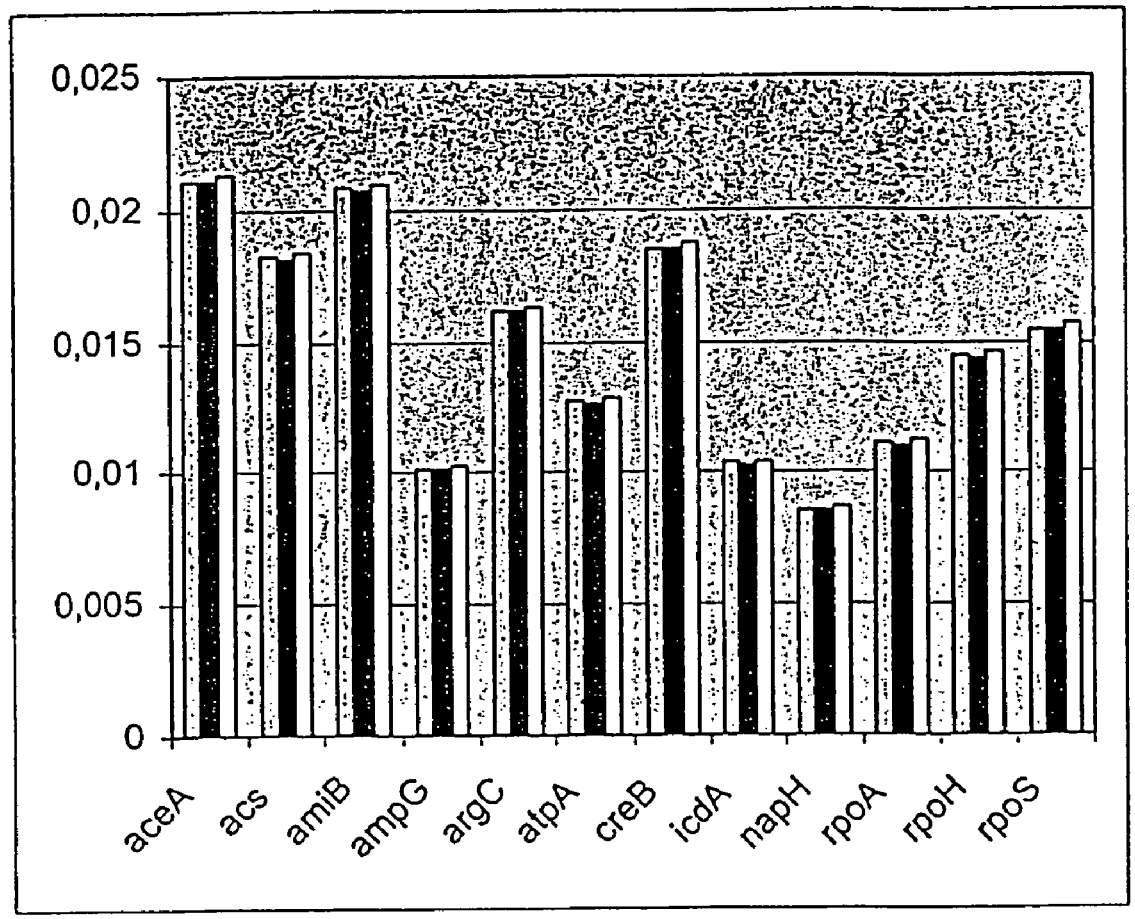
FIG. 6B is a graphical illustration of standardized intensity stages of different regions (three bars) for various PCR products spotted and hybridized with cDNA.

The three bars of cDNA represent referencing of the signal data of hybridisation to three different regions of the standard, with the intensity of said regions differing. To this effect, the results were standardised to the different intensity stages and, taking into account the content of the polymer layers, were calculated to one step. The diagram (FIG. 6B) shows that such back calculation is permissible, because the same results are obtained for each cDNA, irrespective of the region to which the reading of cDNA is related. Thus, if the content of the polymer layers is known, it is permissible to use each region for referencing. This increases the universality of the standard. Readings were obtained with the use of a confocal biochip scanner Scanarray 4000 (Packard) at 100% laser output and 85% PMT gain.

DESCRIPTION OF THE FIGURES

FIG. 1

Production of a fluorescence calibration standard according to the invention by way of multistage photolithography (negative process).

FIG. 2A

Fluorescence calibration standard according to the invention in array-form, microlithographically produced on borofloat glass.

FIG. 2B

Fluorescence calibration standard according to the invention in array form, produced by spotting on borofloat glass.

FIG. 3

Fluorescence calibration standard on a microscope slide.

FIG. 4A

Changes in the resulting luminescence intensity as a result of the effect of irradiation in the visible range (bleaching). The intensity is shown as a greyscale value.

FIG. 4B

Change in the fluorescence intensity over the number of readings in a white-light/CCD system after carrying out a matched tempering protocol. The intensity is shown as a greyscale value.

FIG. 4C

With the use of matched tempering protocols, it is possible to adjust the bleaching behaviour of the polymer layers such that changes in the fluorescence yield over the number of readings carried out have no influence on the resulting intensity ratio. The upper line shows the d3/d2 ratio, while the lower line shows the d2/d1 ratio from FIG. 4A.

FIG. 5

Measurement results of a scan for various dyes. The intensity is shown as a greyscale value. These standards are suitable for standardising results in different wavelength ranges.

FIG. 6A

Inverse scan of a spotted probe array. The fluorescence calibration standard (1) is shown in the upper part. The probe array (2) is below it. These are spotted PCR products after hybridisation with cDNA marked with Cy3/Cy5.

FIG. 6B

Various PCR products were spotted and hybridised with cDNA. The results were standardised to the different intensity stages of different regions (in each instance the three bars) and calculated to one step, taking into account the content of the substances in the polymer layers The diagram shows that such back calculation is permissible. Thus, when the content is known, it does not matter which region is used for standardisation.

What is claimed is:

1. A device for referencing fluorescence signals, comprising:
   an essentially non-fluorescent carrier;
   a plurality of polymer layers applied to the carrier, at least one polymer layer applied to defined regions of the carrier; and
   a plurality of biological probe molecules immobilized with respect to the carrier and configured to interact with a biological target molecule;

wherein:
   the at least one polymer layer fluoresces in response to corresponding irradiation, and wherein at least two of the polymer layers differ with regard to their thickness and/or composition.

2. The device of claim 1, wherein the polymer layers comprise one or more polymers, and wherein at least one of the polymers fluoresces in response to corresponding irradiation.

3. The device of claim 2, wherein the polymers comprise positive photosensitive coatings and/or negative photosensitive coatings.

4. The device of claim 1, wherein the polymer layers comprise fluorescent substances.

5. The device of claim 4, wherein the fluorescent substances comprise at least one of organic dyes and inorganic dyes.

6. The device of claim 1, wherein the intensity of the fluorescence is adjustable by selecting one or more of the layer thickness and the composition of the polymer layers.

7. The device of claim 6, wherein the intensity of the fluorescence is adjustable proportionally to the thickness of the polymer layers applied in the defined regions.

8. The device of claim 1, wherein the intensity of the fluorescence is adjustable by physical treatment methods during the manufacture process, wherein the physical treatment methods include irradiation treatment and temperature treatment.

9. The device of claim 1, wherein the excitation wavelength range of the polymer layers is adjustable by the selection of the polymers.

10. The device of claim 1, wherein, the fluorescence occurring in the defined regions after corresponding irradiation over an extended period, has a bleaching behavior that is adjustable by the selection of at least one of the kind, the quantity, and the composition of the polymer.

11. The device of claim 1, wherein the fluorescence occurring in the defined regions after corresponding irradiation over an extended period, has a bleaching behavior that is adjustable by physical treatment methods during the manufacturing process.

12. The device of claim 1, wherein the maximum thickness of the polymer layers in at least one of the defined regions is significantly smaller than the minimal focal depth of a detection system used for fluorescence measurement.

13. The device of claim 12, wherein the maximum thickness of the polymer layers is between about one nanometer and a max of about 50 μm.

14. The device of claim 1, wherein the defined regions differ in at least one of shape and size.

15. The device of claim 14, wherein the defined regions have a substantially rectangular shape with side lengths between about one nanometer and about 5 mm.

16. The device of claim 14, wherein the defined regions have a substantially circular shape with a diameter between about one nanometer and about 5 mm.

17. The device of claim 1, wherein the defined regions are applied in array form on the carrier.

18. The device of claim 1, wherein the carrier comprises essentially non-fluorescent materials including at least one of glass, metalized glass, silicium, metal, and plastic.

19. The device of claim 18, wherein the carrier comprises essentially non-fluorescent materials with optical transmittance, and wherein the materials include at least one of quartz glass, borofloat glass; polymethyl methacrylate (PMMA), and polycarbonate.

20. The device of claim 1, wherein the device comprises at least one fluorescence calibration standard and is attached to an essentially non-fluorescent carrier system, and wherein the carrier system comprises at least one of glass, metalized glass, silicium, metal, and plastic.

21. The device of claim 20, wherein the essentially non-fluorescent carrier system has optical transmittance, and wherein the carrier system includes at least one of quartz glass, borofloat glass, PMMA, and polycarbonate.

22. The device of claim 21, wherein the carrier system is a microscope slide.

23. The device of claim 1, wherein the plurality of biological probe molecules are arranged in the form of a probe array.

24. The device of claim 23, wherein the biological probe molecules include at least one of peptides and proteins.

25. The device of claim 23, wherein the biological probe molecules include nucleic acid molecules.

26. The device of claim 1, wherein at least one of cells, tissue slices, pharmaceutically active compounds, and plasmids are immobilized on the carrier.

27. A method of manufacturing a device for referencing fluorescence signals, comprising:
applying at least one polymer layer to at least one defined region of an essentially non-fluorescent carrier using a microtechnical process, wherein the at least one polymer layer fluoresces in response to corresponding irradiation; and
immobilizing a plurality of biological probe molecules with respect to the carrier.

28. The method of claim 27, wherein the at least one polymer layer is applied to the carrier by positive or negative photolithographic methods.

29. The method of claim 27, wherein the at least one polymer layer is applied to the carrier as a homogenic layer.

30. The method of claim 27, wherein the thickness of the polymer layer is dependent upon the parameters of the application process, and wherein the parameters include at least one of the viscosity of the polymer, the temperature, the atmospheric humidity, and the circulation speed.

31. The method of claim 27, wherein the geometric form of the defined regions is determined by corresponding recesses in a mask.

32. The method of claim 27, wherein, when more than one polymer layer is applied, cross-linking behavior of the polymer layers is adjustable by tempering and/or irradiation protocols.

33. The method of claim 27, further comprising combining the device with an essentially non-fluorescent carrier system, by way of at least one of adhesion, position adjustment, and a vacuum system.

34. A method of online calibration of fluorescence detection systems with regard to at least one of their spatial or temporal resolution, their geometric and/or dynamic characteristics, and their characteristics caused by aging, comprising:
irradiating a device including:
an essentially non-fluorescent carrier;
a plurality of polymer layers applied to the carrier, at least one polymer layer applied to defined regions of the carrier; and
a plurality of biological probe molecules immobilized with respect to the carrier and configured to interact with a biological target molecule;
wherein the at least one polymer layer fluoresces in response to corresponding irradiation, and wherein at least two of the polymer layers differ with regard to their thickness and/or composition; and
measuring fluorescence from the at least one polymer layer.

35. The method of claim 34, wherein irradiating comprises at least one of measuring and/or regulating laser power, measuring lamp power and/or alignment of integration time, and resolution adaptation.

36. The method of claim 34, wherein measuring fluorescence comprises flat field determination and/or linearization of CCD reader systems.

37. The method of claim 34, further comprising cross-system and/or cross-device comparison of fluorescent signals by standardizing the experimental results to resulting intensities of the polymer layers.

38. The method of claim 34, further comprising quantifying fluorescence signals by standardizing the experimental results to the resulting intensities of the polymer layers for defining absolute results or for defining relative results based on the fluorescence of the polymer layers.

39. The method of claim 34, wherein the fluorescence signals are from protein-protein-interaction studies including at least one of antibody-antigene and/or receptor-ligand interaction studies, nucleic acid-nucleic acid interaction studies, DNA-RNA and/or DNA-DNA and/or RNA-RNA interaction studies, and protein-nucleic acid interaction studies.

40. A method of cross-system and cross-device and/or cross-test comparison of cellular localization experiments and tissue slices which are evaluable by fluorescence microscopy, comprising:
irradiating a device including:
an essentially non-fluorescent carrier;
a plurality of polymer layers applied to the carrier, at least one polymer layer applied to defined regions of the carrier, and
a biological sample including a cell or a tissue slice immobilized with respect to the carrier;
wherein the at least one polymer layer fluoresces in response to corresponding irradiation, and wherein at least two of the polymer layers differ with regard to their thickness and/or composition; and
measuring fluorescence from the at least one polymer layer.

41. A fluorescence calibration device, comprising:
an essentially non-fluorescent carrier having one or more defined regions;
at least one polymer layer applied to the one or more defined regions; and
a plurality of biological probe molecules immobilized with respect to the carrier and configured to interact with a biological target molecule;
wherein the polymer layer is uniform with regard to layer thickness and composition, such that the one or more defined regions fluoresce after corresponding irradiation.

42. The device of claim 3, wherein the polymers are based on epoxy resins including at least one of SU8, novolak, PMMA, photosensitive polyimide, and benzocyclobutene.

43. The device of claim 5, wherein the organic dyes include at least one of an azo dye, a triphenyl methan dye, a porphynine dye and a perylene derivative, and wherein the inorganic dye includes a metallic dye and a lanthanide.

44. The device of claim 4, wherein the excitation wavelength range of the polymer layers is adjustable by the selection of the fluorescent substances.

45. The device of claim 4, wherein the fluorescence occurring in the defined regions after corresponding irradiation over a extended period, has a bleaching behavior that is adjustable by the selection of at least one of the kind, the quantity, and the composition of the fluorescent substances.

46. The device of claim 11, wherein the physical treatment methods include at least one of an irradiation treatment and a temperature treatment.

47. A device, comprising:
a support;
a plurality of spaced-apart polymer masses each being immobilized with respect to the support; and
a plurality of biological probe molecules immobilized with respect to the support;
wherein each of the polymer masses is configured to emit, at a common predetermined wavelength, a respective, different fluorescence intensity when irradiated with light; and the biological probe molecules are configured to interact with a biological target molecule.

48. The device of claim 47, wherein the plurality of biological probe molecules are arranged in the form of a probe array.

49. The device of claim 48, wherein the biological probe molecules include at least one of peptides and proteins.

50. The device of claim 48, wherein the biological probe molecules include nucleic acid molecules.

51. The device of claim 47, wherein the intensity of the fluorescence is adjustable by selecting the thickness of the polymer masses, the composition of the polymer layers, or both.

52. A device for referencing fluorescence signals, comprising:
an essentially non-fluorescent carrier; and
a plurality of polymer layers applied to the carrier, at least one polymer layer applied to defined regions of the carrier; and
wherein:
the at least one polymer layer fluoresces in response to corresponding irradiation, and wherein at least two of the polymer layers differ with regard to their thickness and/or composition,
wherein the intensity of the fluorescence is adjustable by selecting one or more of the layer thickness and the composition of the polymer layers.

53. A method of manufacturing a device for referencing fluorescence signals, comprising:
applying at least one polymer layer to at least one defined region of an essentially non-fluorescent carrier using a microtechnical process, wherein the at least one polymer layer fluoresces in response to corresponding irradiation,
wherein the at least one polymer layer is applied to the carrier by positive or negative photolithographic methods.

* * * * *